United States Patent
Das et al.

(10) Patent No.: US 11,373,757 B2
(45) Date of Patent: Jun. 28, 2022

(54) METHOD AND SYSTEM FOR CLASSIFYING PHONOCARDIOGRAM SIGNAL QUALITY

(71) Applicant: Tata Consultancy Services Limited, Mumbai (IN)

(72) Inventors: Deepan Das, Kolkata (IN); Rohan Banerjee, Kolkata (IN); Anirban Dutta Choudhury, Kolkata (IN); Parijat Dilip Deshpande, Pune (IN); Nital Shah, Pune (IN); Vijay Anil Date, Pune (IN); Arpan Pal, Kolkata (IN); Kayapanda Muthana Mandana, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 1150 days.

(21) Appl. No.: 15/913,682

(22) Filed: Mar. 6, 2018

(65) Prior Publication Data
US 2019/0013102 A1    Jan. 10, 2019

(30) Foreign Application Priority Data

Jul. 10, 2017   (IN) .............................. 201721024202

(51) Int. Cl.
*G08B 21/04* (2006.01)
*G16H 50/20* (2018.01)
(Continued)

(52) U.S. Cl.
CPC ............. *G16H 50/20* (2018.01); *A61B 5/725* (2013.01); *A61B 5/7214* (2013.01);
(Continued)

(58) Field of Classification Search
USPC .... 340/539.12, 538.11, 538.13, 539.24, 575, 340/674, 692, 5.82, 5.83
See application file for complete search history.

(56) References Cited

U.S. PATENT DOCUMENTS 5,623,520 A *  4/1997  Kaiser ................ H04L 27/2332
                                                           708/422
8,686,992 B1 *  4/2014  Makadia .............. G06V 20/653
                                                           345/422

(Continued)

FOREIGN PATENT DOCUMENTS

CA      2 818 790      12/2013
WO   WO-2017/079828    5/2017

OTHER PUBLICATIONS

Das, D. et al. "Noise Detection in Smartphone Phonocardiogram," *2017 IEEE International Conference on Acoustics, Speech and Signal Processing (ICASSP)*, New Orleans, Louisiana, Mar. 5-9, 2017; 2 pages.

(Continued)

*Primary Examiner* — Daniel Previl
(74) *Attorney, Agent, or Firm* — Finnegan, Henderson, Farabow, Garrett & Dunner LLP

(57) ABSTRACT

A system and method for classifying the phonocardiogram (PCG) signal quality has been described. The system is configured to identify the quality of the PCG signal recording and accepting only diagnosable quality recordings for further cardiac analysis. The system includes the derivation of plurality features of the PCG signal from the training dataset. The extracted features are preprocessed and are then ranked using mRMR algorithm. Based on the ranking the irrelevant and redundant features are rejected if their mRMR strength is less. A training model is generated using the relevant set of features. The PCG signal of the person under test is captured using a digital stethoscope and a smartphone. The PCG signal is preprocessed and only the relevant set of features are extracted. And finally the PCG signal is classified into diagnosable or non-diagnosable using the relevant set of features and a random forest classifier.

16 Claims, 8 Drawing Sheets

(51) Int. Cl.
    A61B 5/00      (2006.01)
    A61B 7/04      (2006.01)
    G06N 20/00     (2019.01)
    A61B 7/00      (2006.01)

(52) U.S. Cl.
    CPC .............. *A61B 5/7267* (2013.01); *A61B 7/00* (2013.01); *A61B 7/04* (2013.01); *G06N 20/00* (2019.01)

(56) References Cited

U.S. PATENT DOCUMENTS

| | | | |
|---|---|---|---|
| 9,978,392 B2* | 5/2018 | Ukil | A61B 5/7221 |
| 10,019,442 B2* | 7/2018 | Nefedov | G06F 16/951 |
| 11,080,336 B2* | 8/2021 | Van Dusen | G06Q 50/01 |

OTHER PUBLICATIONS

Springer, D.B. et al. "Signal Quality Classification of Mobile Phone-Recorded Phonocardiogram Signals," *2014 IEEE International Conference on Acoustics, Speech and Signal Processing (ICASSP)*, Florence, IT, May 4-9, 2014; 5 pages.

Messer, S.R. et al. (2001). "Optimal wavelet denoising for phonocardiograms," *Microelectronics Journal*, vol. 32; pp. 931-941.

* cited by examiner

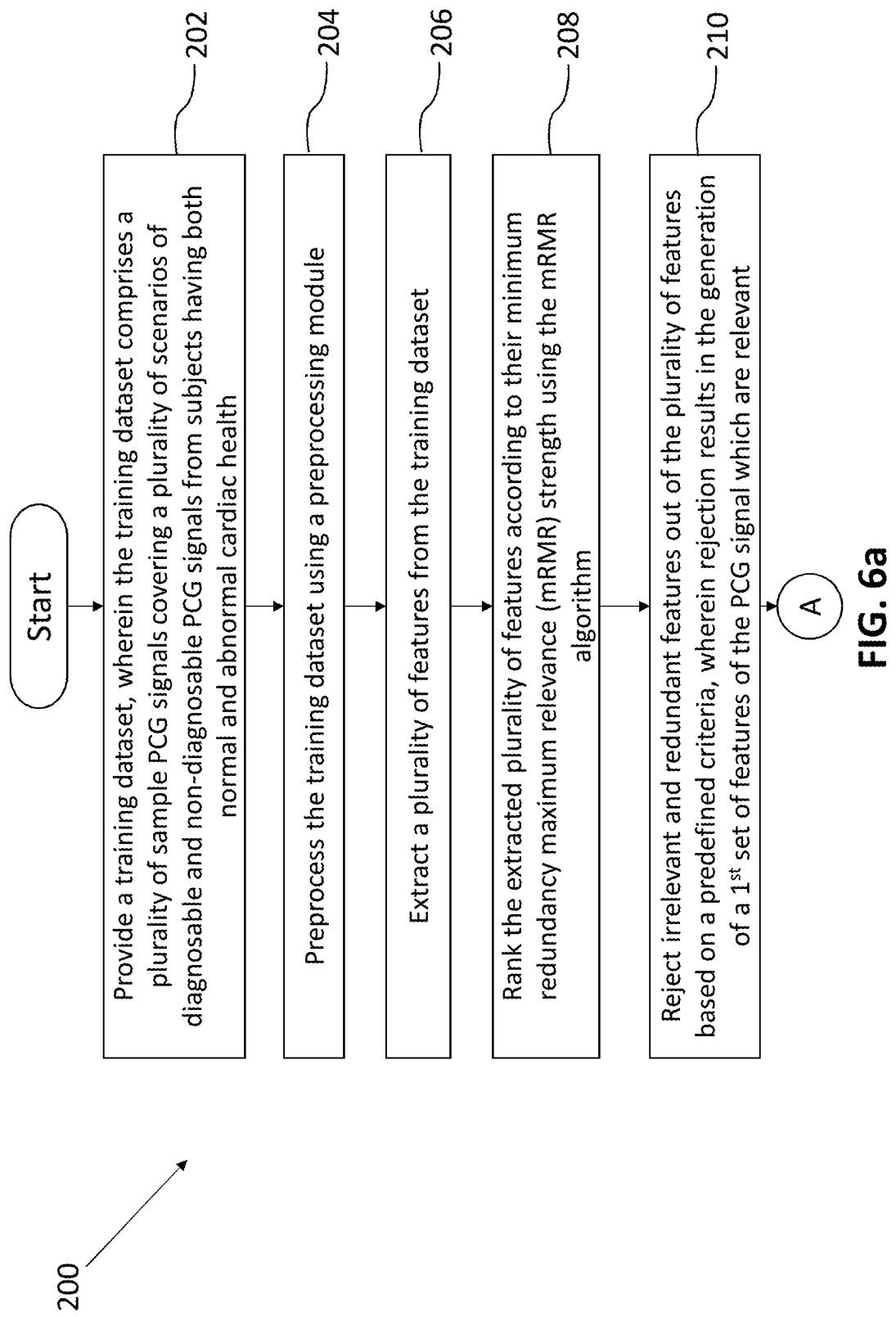

METHOD AND SYSTEM FOR CLASSIFYING PHONOCARDIOGRAM SIGNAL QUALITY

PRIORITY CLAIM

This U.S. patent application claims priority under 35 U.S.C. § 119 to: India Application No. 201721024202, filed on Jul. 10, 2017. The entire contents of the aforementioned application are incorporated herein by reference.

TECHNICAL FIELD

The embodiments herein generally relates to the field of cardiac analysis using a phonocardiogram (PCG) signal, and, more particularly, to a method and system for classifying the phonocardiogram (PCG) signal quality as either diagnosable or non-diagnosable.

BACKGROUND

Heart sound signals, commonly known as phonocardiogram (PCG) is typically captured using a digital stethoscope and is known to carry useful information regarding many cardiac abnormalities. With the global proliferation of the smartphones, the smartphones have become a popular choice for deployment of low cost PCG recording systems. But most of the affordable smartphones do not ship with a microphone quality necessary for consistent medical-grade PCG recordings. Further, personnel involved in providing and receiving point-of-care services, are mostly medically untrained. Thus the protocols that must be followed during a PCG recording, are not always strictly adhered to. The above factors lead to background noises, frictional noises between the subject's skin and the recording device, microphone static etc. corrupting the recordings. Additionally, incorrect positioning of the recording device causes the PCG recording to be faint or completely inaudible.

Various prior art techniques have been used in the field to improve the quality of PCG signal captured from the smartphone. Mainly these include manually rejecting noisy portions of PCG or the entire noisy recording prior to analysis. These methods followed the convention of accepting or rejecting relevant portions of data post-recording. The parameters used for estimating quality were largely application specific and often determined by the developers, thus making them unsuitable across systems. In template-matching based research efforts, cardiac cycles were compared to an artefact-free segment considered as a reference. Similarities between the reference segment and individual segments were estimated in both time and time-frequency domains. Another prior art introduced logarithmic energy, noise level variation and variation in certain heart sound (S1, S2) durations as features. But these approaches introduced heuristically determined thresholds on the feature values for decision-making, which may pose an issue of portability across devices, systems and recording environments. A few other prior art have developed a system that assesses the PCG quality based on expert annotation regarding diagnosable quality. However it was limited in terms of diversity in devices and patient cardiac conditions.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

In another aspect, the disclosure provides a method for classifying phonocardiogram (PCG) signal quality. Initially, a training dataset is provided to the processor, wherein the training dataset comprises a plurality of sample PCG signals covering a plurality of scenarios of diagnosable and non-diagnosable PCG signals from subjects having both normal and abnormal cardiac health. The training dataset is then preprocessed using a preprocessing module. In the next step, a plurality of features are extracted from the training dataset. The extracted plurality of features are then ranked according to their minimum redundancy maximum relevance (mRMR) strength using an mRMR algorithm. In the next step, the irrelevant and redundant features are rejected out of the plurality of features based on a predefined criteria, wherein the remaining features form a first set of features of the PCG signal which are relevant. Later, a training model is generated using the first set of features. In the next step, the phonocardiogram (PCG) signal is captured from a person under test using a PCG sensor. The PCG signal is then preprocessed using the preprocessing module. In the next step, the first set of features are extracted from the preprocessed PCG signal. And finally the PCG signal is classified as diagnosable or non-diagnosable using the first set of features and a random forest classifier, wherein the random forest classifier is pre-trained using the training model.

In view of the foregoing, an embodiment herein provides a system for classifying phonocardiogram (PCG) signal quality, the system comprises a memory, a processor, a PCG sensor and a classification module. The processor further comprises an input module, a preprocessing module, a feature extraction module, a ranking module and a training model generation module. The input module provides a training dataset, wherein the training dataset comprises a plurality of sample PCG signals covering a plurality of scenarios of diagnosable and non-diagnosable PCG signals from subjects having both normal and abnormal cardiac health. The preprocessing module preprocesses the training dataset. The feature extraction module extracts a plurality of features from the training dataset. The ranking module ranks the extracted plurality of features according to their minimum redundancy maximum relevance (mRMR) strength using an mRMR algorithm, the ranking module further configured to reject the irrelevant and redundant features out of the plurality of features based on a predefined criteria, wherein the remaining features form a first set of features of the PCG signal which are relevant. The training model generation module generates the training model using the first set of features. The PCG sensor captures the phonocardiogram (PCG) signal from a person under test, wherein the PCG signal preprocessed using the preprocessing module, and the first set of features are extracted from the preprocessed PCG signal. The classification module classifies the PCG signal as diagnosable or non-diagnosable using the extracted first set of features and a random forest classifier, wherein the random forest classifier is pre-trained using the training model.

In view of the foregoing, another embodiment herein provides a system for monitoring the cardiac health using a phonocardiogram (PCG) signal of a person. The system comprises a memory, a processor, a PCG sensor, a classification module and a cardiac health detection module. The processor further comprises an input module, a preprocessing module, a feature extraction module, a ranking module and a training model generation module. The input module provides a training dataset, wherein the training dataset comprises a plurality of sample PCG signals covering a plurality of scenarios of diagnosable and non-diagnosable PCG signals from subjects having both normal and abnormal cardiac health. The preprocessing module preprocesses the training dataset. The feature extraction module extracts a plurality of features from the training dataset. The ranking module ranks the extracted plurality of features according to their minimum redundancy maximum relevance (mRMR) strength using an mRMR algorithm, the ranking module further configured to reject the irrelevant and redundant features out of the plurality of features based on a predefined criteria, wherein the remaining features form a first set of features of the PCG signal which are relevant. The training model generation module generates the training model using the first set of features. The PCG sensor captures the phonocardiogram (PCG) signal from a person under test, wherein the PCG signal preprocessed using the preprocessing module, and the first set of features are extracted from the preprocessed PCG signal. The classification module classifies the PCG signal as diagnosable or non-diagnosable using the extracted first set of features and a random forest classifier, wherein the random forest classifier is pre-trained using the training model. The cardiac health detection module monitors the health of the person using only diagnosable PCG signal as classified by the classification module.

In another embodiment herein provides one or more non-transitory machine readable information storage mediums comprising one or more instructions, which when executed by one or more hardware processors perform actions comprises a memory, a processor, a PCG sensor, a classification module and a cardiac health detection module. The processor further comprises an input module, a preprocessing module, a feature extraction module, a ranking module and a training model generation module. The input module provides a training dataset, wherein the training dataset comprises a plurality of sample PCG signals covering a plurality of scenarios of diagnosable and non-diagnosable PCG signals from subjects having both normal and abnormal cardiac health. The preprocessing module preprocesses the training dataset. The feature extraction module extracts a plurality of features from the training dataset. The ranking module ranks the extracted plurality of features according to their minimum redundancy maximum relevance (mRMR) strength using an mRMR algorithm, the ranking module further configured to reject the irrelevant and redundant features out of the plurality of features based on a predefined criteria, wherein the remaining features form a first set of features of the PCG signal which are relevant. The training model generation module generates the training model using the first set of features. The PCG sensor captures the phonocardiogram (PCG) signal from a person under test, wherein the PCG signal preprocessed using the preprocessing module, and the first set of features are extracted from the preprocessed PCG signal. The classification module classifies the PCG signal as diagnosable or non-diagnosable using the extracted first set of features and a random forest classifier, wherein the random forest classifier is pre-trained using the training model. The cardiac health detection module monitors the health of the person using only diagnosable PCG signal as classified by the classification module.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

BRIEF DESCRIPTION OF THE DRAWINGS

The embodiments herein will be better understood from the following detailed description with reference to the drawings, in which:

FIG. 6a-6b is a flowchart illustrating the steps involved for classifying a phonocardiogram (PCG) signal quality according to an embodiment of the present disclosure.

DETAILED DESCRIPTION OF EMBODIMENTS

Figure 1:
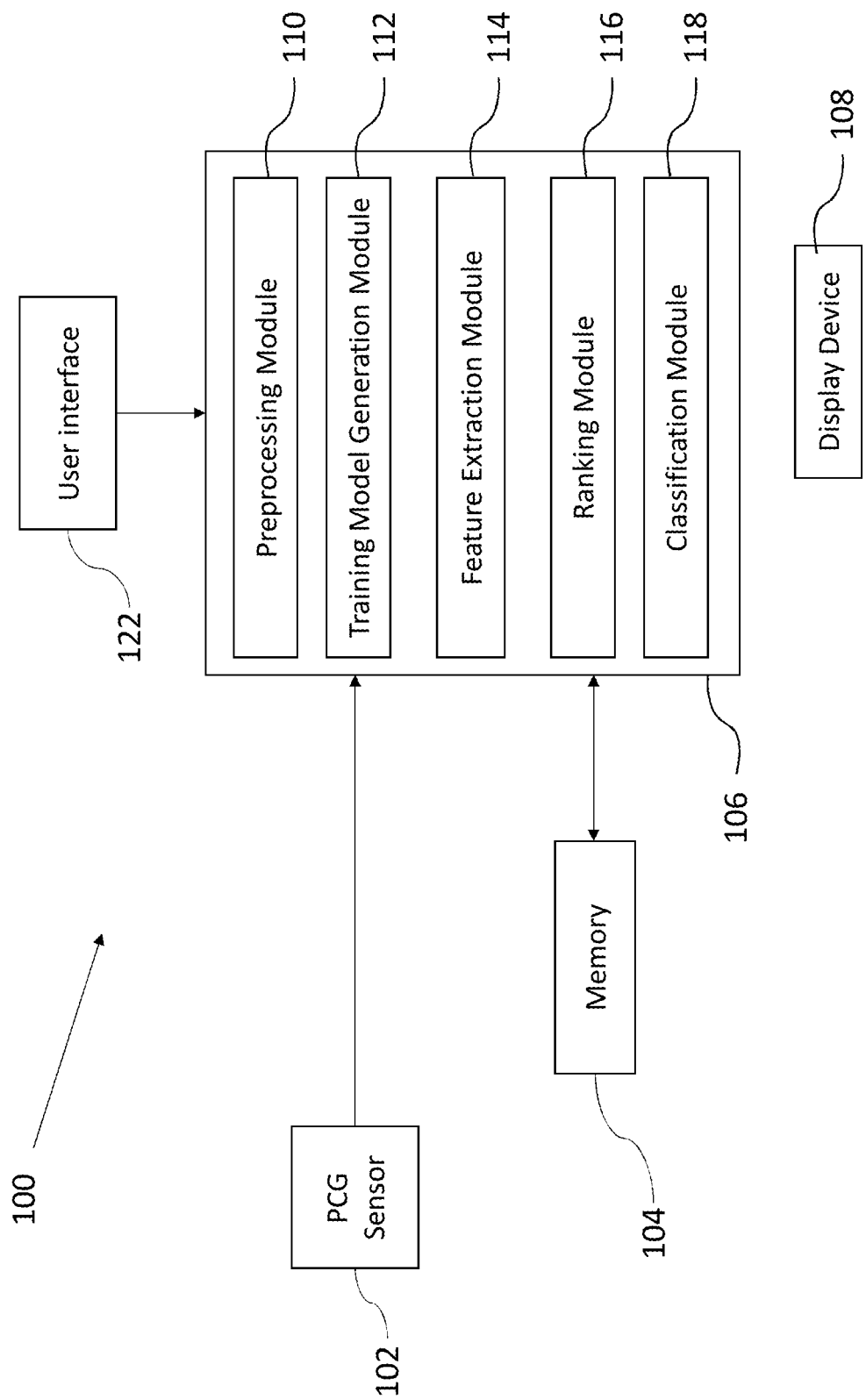
FIG. 1 illustrates a block diagram for classifying a phonocardiogram (PCG) signal quality according to an embodiment of the present disclosure.

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Glossary—Terms Used in the Embodiments

The expression "phonocardiogram" or "PCG" in the context of the present disclosure refers to the signal captured from the person using a PCG sensor. The PCG signal typically contains two prominent heart sounds, namely S1 and S2. S1 precedes the systole whereas S2 precedes the diastole region.

Referring now to the drawings, and more particularly to FIG. 1 through FIG. 6, where similar reference characters denote corresponding features consistently throughout the figures, there are shown preferred embodiments and these embodiments are described in the context of the following exemplary system and/or method.

According to an embodiment of the disclosure, a system 100 for classifying a phonocardiogram (PCG) signal quality is shown in FIG. 1. The system 100 is configured to identify the quality of the PCG signal recording and accepting only diagnosable quality recordings for further cardiac analysis. The system 100 includes the derivation of novel features of the PCG signal which are used to identify the quality of the PCG signal in real time. The system 100 also sends a real time feedback to a user, thus ensuring that the user can correctly reposition the stethoscope attachment such that the captured PCG signal are of a consistently good quality.

According to an embodiment of the disclosure, the system 100 consists of a phonocardiogram (PCG) sensor 102, a memory 104, a processor 106 and a display device 108 as shown in the block diagram of FIG. 1. The processor 106 is in communication with the memory 104. The processor 106 configured to execute an algorithm stored in the memory 104. The processor 106 further comprises a plurality of modules for performing various functions. The processor 106 comprises a preprocessing module 110, a training model generation module 112, a feature extraction module 114, a ranking module 116, and a classification module 118.

Figure 2:
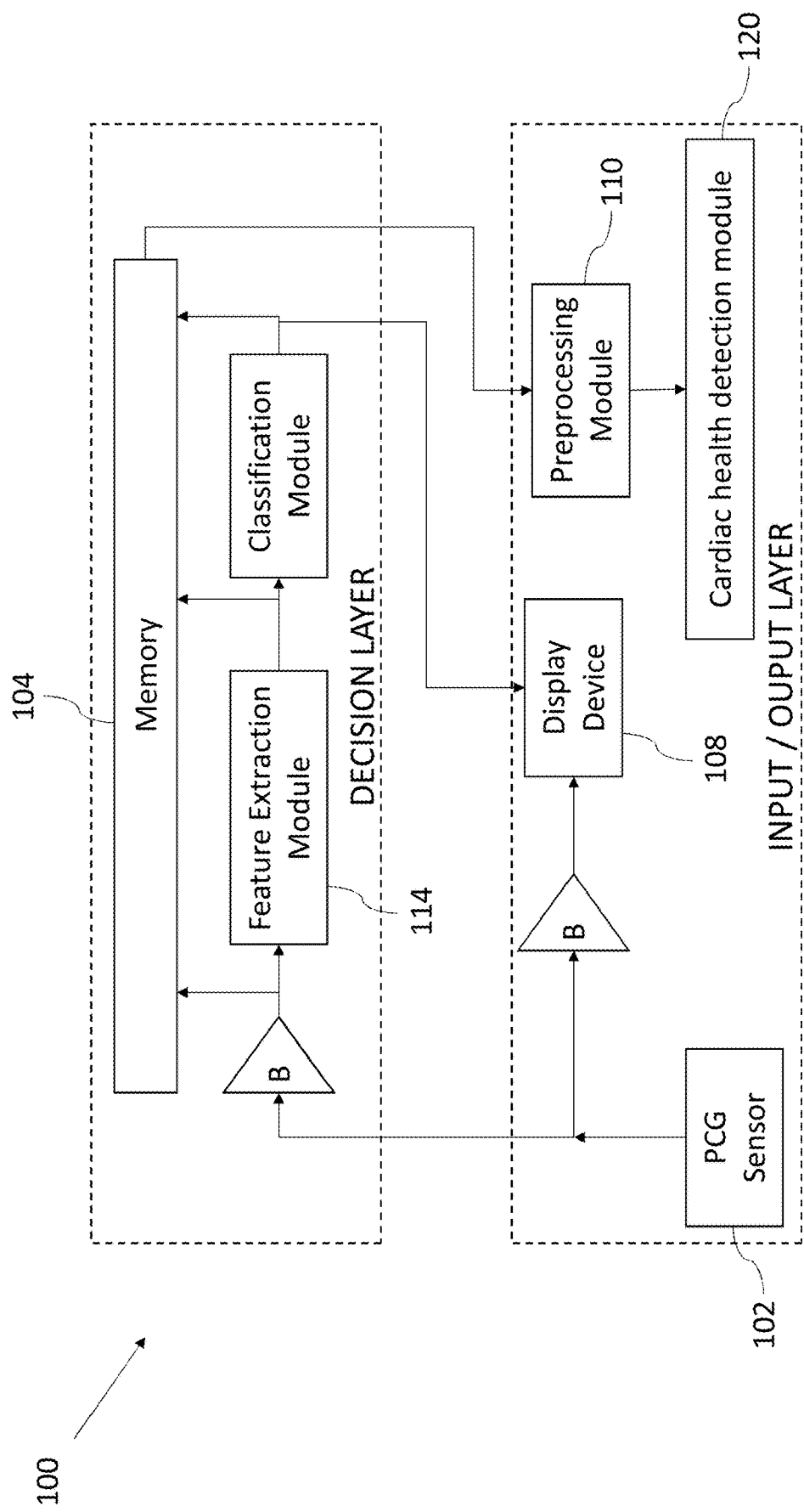
FIG. 2 illustrates an architecture of cardiac health monitoring system according to an embodiment of the disclosure.
Figure 3:
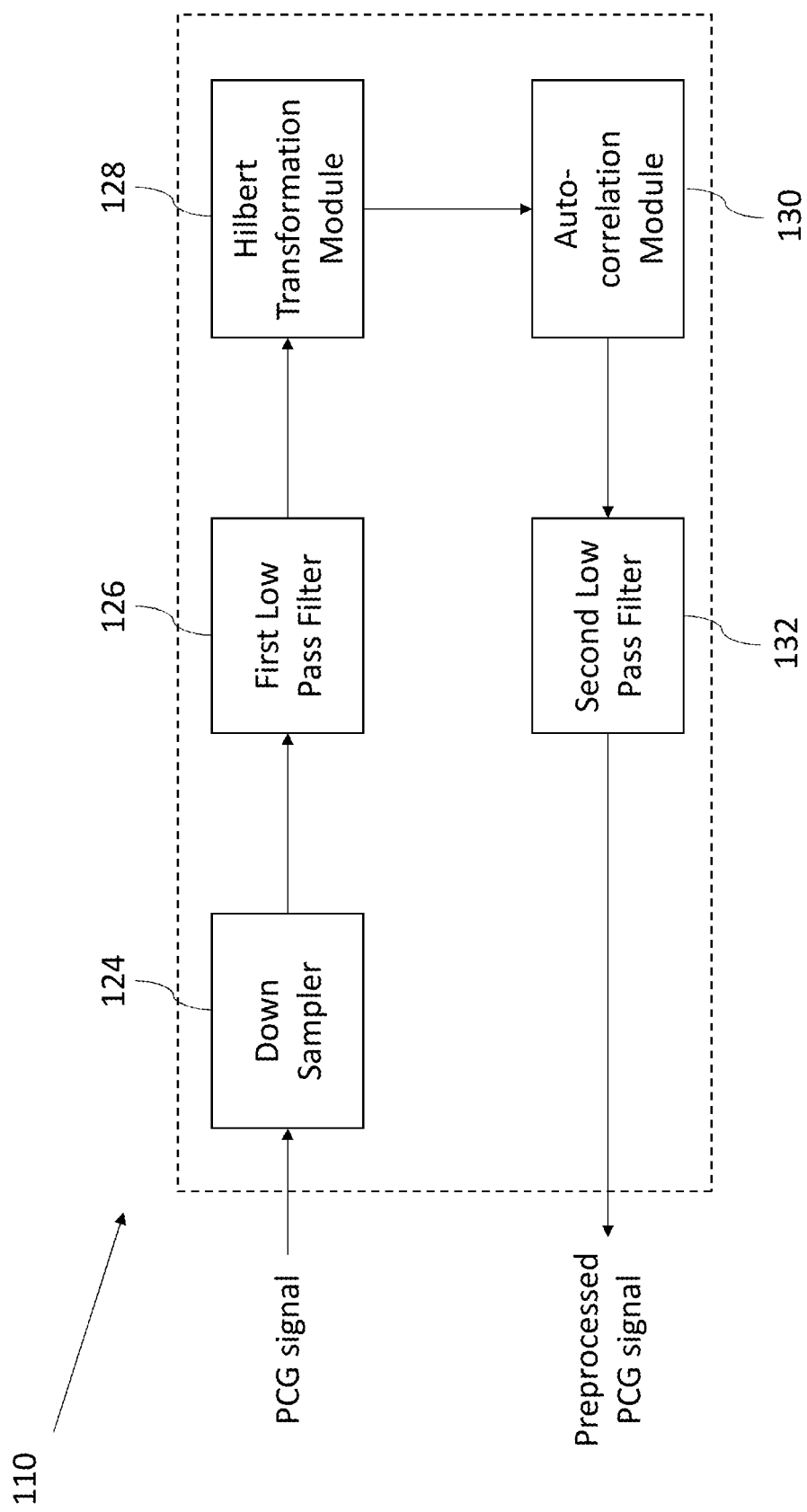
FIG. 3 illustrates an illustrative block diagram of a preprocessor according to an embodiment of the present disclosure.

According to an embodiment of the disclosure, the system 100 can further be expanded as a cardiac health monitoring system to detect the cardiac health of the person using only diagnosable PCG signals. The cardiac health monitoring system includes two layers, i.e. a decision layer and an input/output layer as shown in the architecture of FIG. 2. The Boolean output 0/1 denotes the decision made on input PCG signal quality. Output of 0 corresponds to input PCG signal being not diagnosable, while output 1 denotes an input PCG signal of diagnosable quality. The architecture may also include a cardiac health detection module 120. The cardiac heath detection module 120 is configured to automatically detect the cardiac condition of the person using the diagnosable PCG signal provided as an output by the classification module 118 of the system 100.

According to an embodiment of the disclosure, the system 100 may also include an input module 122. The input module 122 can also be a user interface 122. The user interface 122 is configured to provide various inputs to the system 100. The inputs can be training dataset or any other related data. The user interface 122 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the user interface 122 can include one or more ports for connecting a number of devices to one another or to another server.

According to an embodiment of the disclosure, the system 100 takes two inputs, a testing data and a training data. The testing data may also be referred as the PCG signal captured from a user under test. The PCG signal can be captured using the PCG sensor 102. The use of any available PCG sensor is well within the scope of this disclosure. Though in an embodiment, the PCG signal was captured on a Nexus 5 smartphone using a low-cost stethoscope attachment. A data logger application was used to dump raw audio data at 8 KHz sampling frequency. Data annotations were made by amalgamating the independent opinions of multiple expert clinicians, possessing high inter-rater agreement. Clean to noisy for 20 recordings is 2:3.

According to an embodiment of the disclosure the training data is provided using the input module 122. The training data include a plurality of sample PCG signals covering a plurality of scenarios of diagnosable and non-diagnosable PCG signals from subjects having both normal and abnormal cardiac health. In an example, the training data is taken from the PCG signal dataset made public by organizers of the Physionet Challenge, 2016. This dataset exhibits the requisite diversity in various parameters of recording device (various off-the-shelf electronic stethoscopes), recording environment and subject demographics. 2664 PCGs, from 658 subjects belonging to 6 different geographies, are distributed over classes clean (diagnosable) and noisy (not diagnosable) in the ratio 16:1. The use of any other database is well within the scope of this disclosure.

According to an embodiment of the disclosure the system 100 includes the preprocessing module 110. The preprocessing module 110 is configured to preprocess the training dataset and the testing data. The preprocessing module 110 further includes a down sampler 124, a first low pass filter 126, a Hilbert transformation module 128, an auto correlation module 130 and a second low pass filter 132. The preprocessing module 110 is configured to remove the noise from the PCG signal.

The PCG signal either from the PCG sensor 102 or from the training dataset is provided as the input to the preprocessing module 110. Initially the PCG signal is down sampled using the down sampler 124. The envelope of the down sampled PCG signal is then estimated by filtering it through the first low pass filter 126. The first low pass filter 126 is a 2nd order Butterworth low-pass filter at frequency of about 20 Hz. The filtered signal is then transformed using the Hilbert transformation module 128. The transformed PCG signal is then provide to the auto correlation module 130. The auto correlation module 130 calculates the auto-correlation waveform of the transformed PCG signal. The auto correlated PCG signal is then low-pass filtered using the second low pass filter 132 at 10 Hz. The second low pass filter 132 is a $2^{nd}$ order Butterworth filter. The backward-forward filtering ensured zero-phase distortion.

Figure 4:
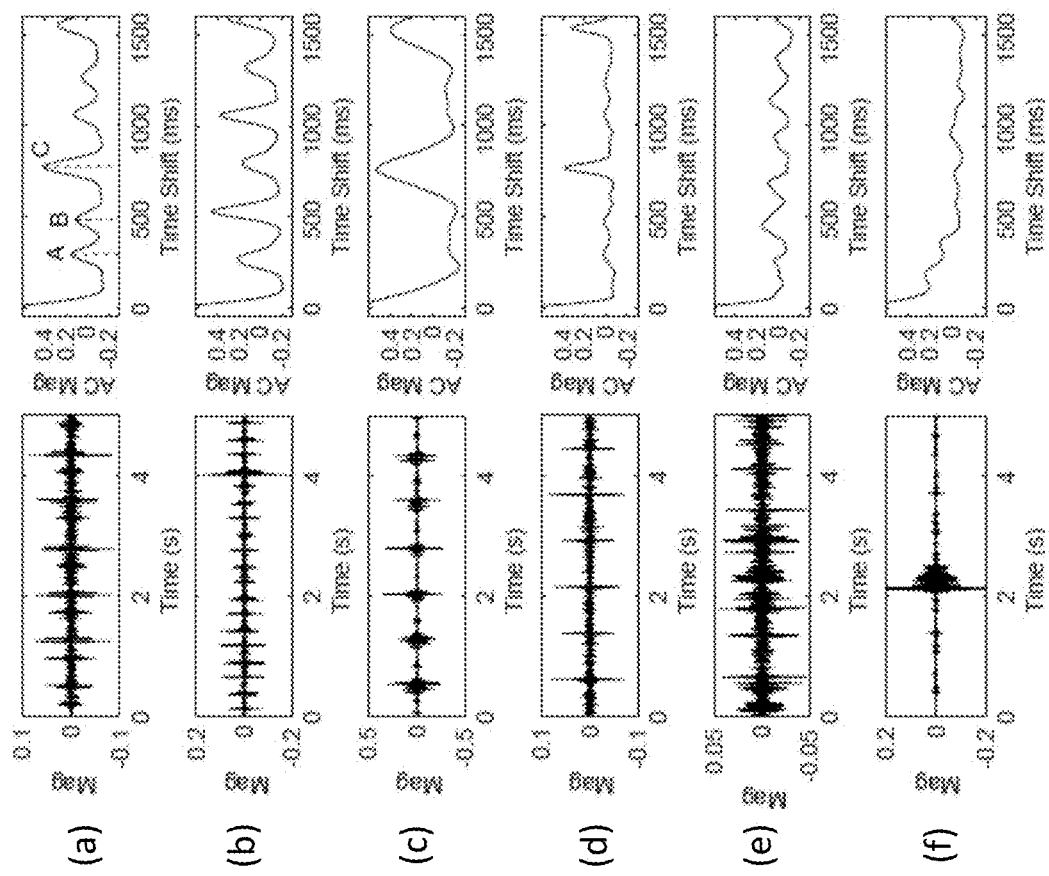
FIG. 4 shows different kinds of raw PCG waveforms and their final autocorrelation waveforms according to an embodiment of the disclosure.

According to an embodiment of the disclosure, the final waveforms are illustrated in FIG. 4 along with the raw recordings. FIG. 4 shows different kinds of raw PCG (1-3 clean where all heart sounds are audible, 4-5 moderately noisy and 6 noisy where one or more heart sounds are inaudible) and their final autocorrelation waveforms. The illustrated waveform patterns are obtained because a PCG is quasi-periodic while noise is non-stationary. The waveform for clean and normal PCG in FIG. 4(a) has peaks at shifts equal to (A) systolic, (B) diastolic and (C) cardiac cycle durations.

According to an embodiment of the disclosure, the system 100 includes the feature extraction module 114. The feature extraction module 114 is configured to extract a plurality of feature from the preprocessed training dataset. The plurality of features may either include features derived from the auto-correlated PCG signal or the spectral features derived from the input PCG signal. In an example of the present embodiment following set of features have been used. Table 1 shows the features derived from the Auto-correlated PCG signal, while the Table 2 shows the spectral features derived from the PCG signal.

TABLE 1

| Index | Description |
| --- | --- |
| 1 2 3 4 | Sample entropy of final waveform [10] |
| 5 | Kurtosis of final waveform [10] |
| 6 | Minimum ratio of the second to first singular value from the singular value decomposition (SVD) of varying window sizes of final waveform [6] |
| 7 | Signal power of final waveform [10] |
| 9 | Variance of final waveform [10] |

TABLE 1-continued

| Index | Description |
|---|---|
| 10 11 12 | Correlation coefficient between final waveform and a fitted sum of 1, 2 or 3 rectified sinusoids, FIG. 3(a) 3(b) 3(c). Feature 10 is adopted from [10] (Algorithm 1) |
| 13 14 15 | Correlation coefficient between final waveform and a fitted sum of 1, 2 or 3 rectified and decaying sinusoids, FIG. 3(d) 3(e) 3(f) (Algorithm 1) |

TABLE II

| Index | Description |
|---|---|
| 8 | Ratio of power contained in 0-240 Hz to the power contained in 240-1000 Hz [10] |
| 16 17 | Mean and variance of ratio of power contained in 0-500 Hz to the remaining power for overlapping frames |

Features numbered 1 to 10 has been derived using well known method in the art. The feature number 11 to 15 were developed as an extension of feature numbered 10. The extraction of these five features, along with feature number 10, is described in Algorithm 1 as follows:

Algorithm 1 Fitting rectified sinusoids for feature no. 10-15

```
1:  procedure FIT(ac,minsep)
        ▷ ac : Final autocorrelation waveform
        ▷ minsep : minimum separation, typically 50 ms
2:      peak_locs, peak_heights = peakdetect(ac,minsep)
3:      for all peak_locs do
4:          a ← peak_heights  b ← peak_locs
5:          for all j ∈ ⟨1,2,3⟩ do
6:              signal_j = a × Σ_{k∈S} COS (k)
7:              signal_{j+3} = signal_j × exp(log | b | /a × t)
8:          end for
9:          ρ_j = corr(rect(signal_j), ac) for j ∈ ⟨1, ..., 6⟩
10:     end for
11: end procedure
```

The underlying assumption behind feature 10 was that that clean PCG signals produced autocorrelation waveforms conforming to the pattern shown in FIG. 4(a), with peak C being consistently far more prominent than peaks A and B. However, as illustrated in the remaining waveforms in FIGS. 4(b) to 4(e), such is not always the case for clean PCG signals. Presence of cardiac abnormalities, variations in frequency response and thermal noise of the recording device, presence of acceptable levels of ambient noise etc. cause deviations from the pattern of FIG. 4(a). Feature 10 was found to be biased such that it led to high rejection of PCGs exhibiting the aforementioned deviations. The new features, numbered 11 to 15, were introduced to address this particular bias.

Figure 5:
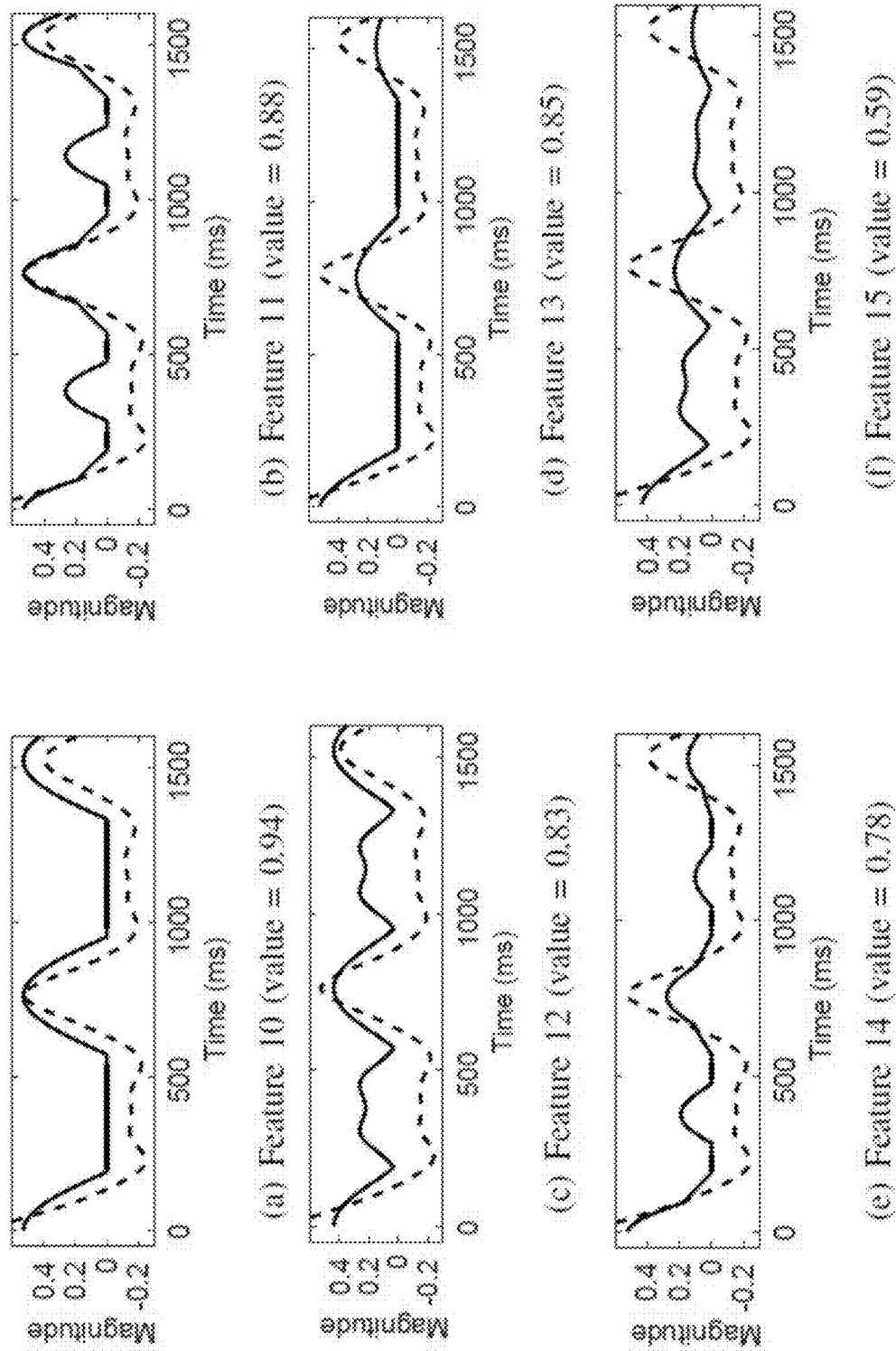
FIG. 5 shows the correlation coefficient calculated between the final waveform obtained from PCG and synthetic, fitted waveforms for different features, with the corresponding feature values listed according to an embodiment of the disclosure.

In Algorithm 1, set S is defined such that for j ε(1,2,3), k varies over 1, 2 or 3 values respectively with each value being of the form $(2\pi)/b+\phi$. The peak producing consistently high values of p is considered peak C (FIG. 4(a)). Some fitted waveforms are illustrated in FIG. 5. These variations are covered to account for the deviation of autocorrelation waveforms of different clean but abnormal PCGs (FIGS. 4(b) to 4(e)) from the ideal pattern of FIG. 4(a).

Abnormal and normal PCGs have variable components ranging from 20-500 Hz. Most of their power is concentrated in this frequency band. The PCG signal is divided into 2 s segments with 0.5 s overlap. Mean and variance of ratio of power in 0-500 Hz to power in 500-1000 Hz are both expected to be higher in clean signals because of a lower noise floor. An essential part of the solution is the selection of an optimum feature set, by rejecting redundant features, reducing computation time, producing high performance scores and maintaining low performance variation.

According to an embodiment of the disclosure, the system 100 further includes the ranking module 116. The ranking module 116 is configured to rank the extracted plurality of features according to their minimum redundancy maximum relevance (mRMR) strength using an mRMR algorithm. The ranking module (116) further configured to reject the irrelevant and redundant features out of the plurality of features based on a predefined criteria, wherein the remaining features form a first set of features of the PCG signal which are relevant.

In an example of the present embodiment, features, that are ranked low by the mRMR algorithm, are studied further and found to be not truly sensor-agnostic. Thus the first set of feature consists of features numbered 15, 17, 6, 16, 8, 5, 4, 12, 10, 11 and 14.

In the example of present embodiment, each of the plurality of features are ranked according to their Minimum Redundancy Maximum Relevance (mRMR) strength computed against the data class, for each of the 16 (balanced) datasets. A final consolidated ranking is prepared from them. Spearman's Rank Correlation Coefficients between the final rank series and the initial 16 rank series have a mean value 0.85, range [0.76-0.91] and standard deviation 0.04. Thus the final feature rank, reported in Table III, has high degrees of similarity with the initial 16 rank series. Mean and standard deviation of the rank of each feature is provided in the table.

TABLE III

| | Rank | | | | | |
|---|---|---|---|---|---|---|
| | 1 | 2 | 3 | 4 | 5 | 6 |
| Index | 15 | 17 | 6 | 16 | 8 | 5 |
| STD | 0.00 | 1.42 | 1.18 | 1.40 | 1.93 | 3.11 |
| | Rank | | | | | |
| | 7 | 8 | 9 | 10 | 11 | 12 |
| Index | 4 | 11 | 14 | 13 | 12 | 10 |
| STD | 1.72 | 2.28 | 1.34 | 1.33 | 5.09 | 5.35 |
| | Rank | | | | | |
| | 13 | 14 | 15 | 16 | 17 | — |
| Index | 7 | 9 | 3 | 1 | 2 | — |
| STD | 3.07 | 2.91 | 1.36 | 2.53 | 1.82 | — |

According to an embodiment of the disclosure the system 100 includes the training model generation module 112. The training model generation module 112 generates the training model using the first set of features derived from the training dataset.

According to an embodiment of the disclosure, the system 100 further includes the classification module 118. The PCG signal captured from the person under test using the PCG sensor 102 is further used to extract only the first set of features using the feature extraction module 114. Since the first set of features are relevant features thus they are used to as input to the classification module 118.

The classification module 118 is configured to classify the PCG signal as diagnosable or non-diagnosable using the extracted first set of features and a random forest classifier, wherein the random forest classifier is pre-trained using the training model. The aim is to use the training set to develop a universal, robust, sensor-agnostic binary classifier for smartphone PCG quality. The Random Forest classifier was chosen because the main interest was in the proximity of observations in the two classes and interaction between features. The Random Forest classifies observations by nested conditional statements. This makes it easy to port across various systems. It is generally simpler to avoid over-fitting in this approach, since it ensembles a large number of decision trees. It also exhibits performance comparable to or excelling current basic algorithms. Accordingly the Random Forest for classifying noisy and clean data was used, in which the number of trees was 120 and number of features considered for each decision split was square root of total number of features.

Parameters were determined via cross validation on the training data. Given a random environment, recording device, agent and subject, i.e. an unbiased system, a PCG recording has equal chances of being clean or noisy, posteriori probabilities are as 1:1. However, priori probabilities in the training set are found to be in an approximate ratio of 16:1 (2506:157) for clean:noisy. The clean set is partitioned into 16 random, exclusive and exhaustive subsets of equal cardinality. Each such subset is combined with all noisy recordings to create a balanced dataset. Train/Evaluate are carried out within each of these balanced datasets using K-fold (K=5) cross-validation technique. Performance metrics reported throughout are measured across all 5 folds over all 16 datasets.

Figure 6B:
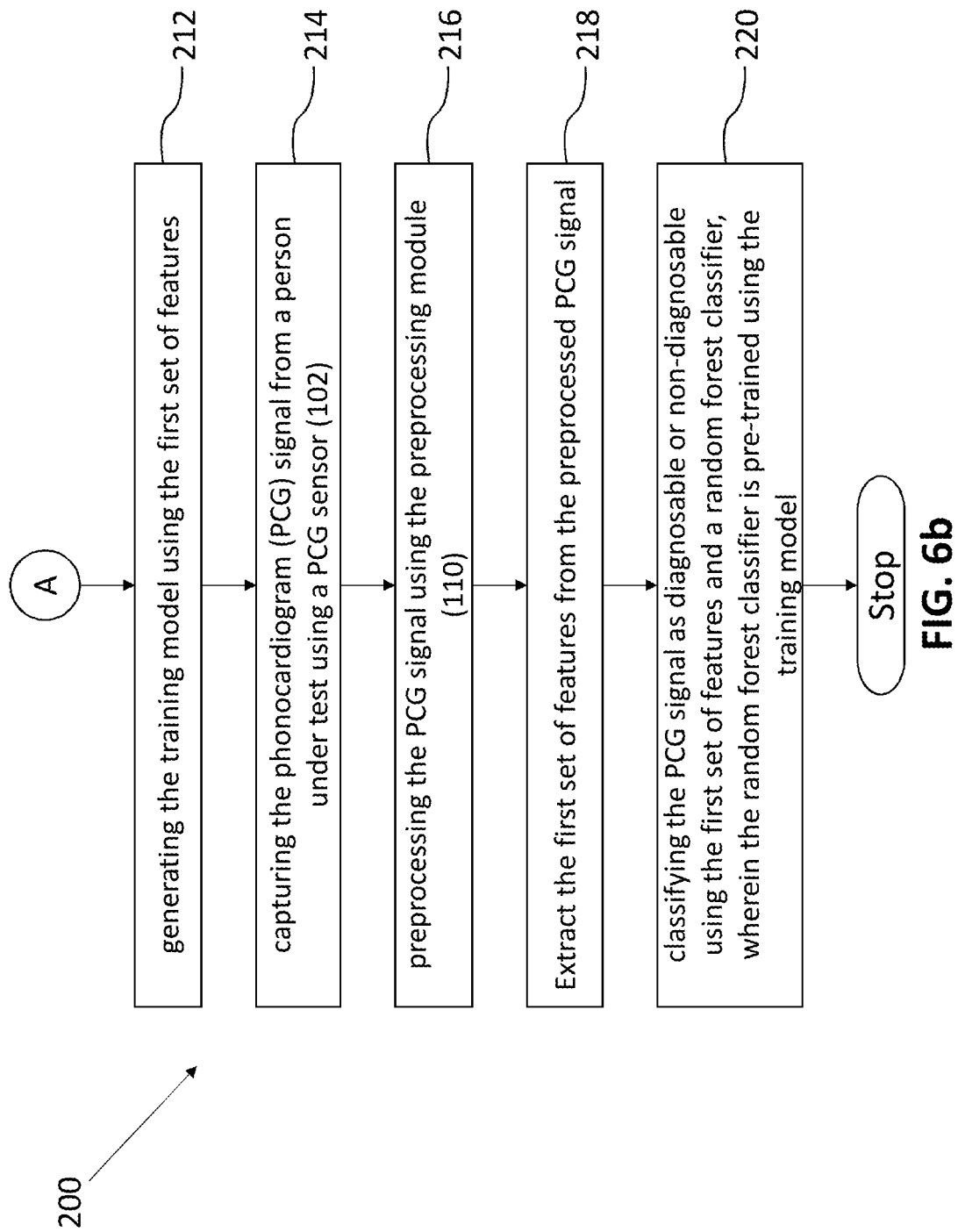

In operation, a flowchart 200 illustrating the steps involved for the classifying phonocardiogram (PCG) signal quality is shown in FIG. 6a-6b. Initially at step 202, a training dataset is provided by the processor. The training dataset comprises a plurality of sample PCG signals covering a plurality of scenarios of diagnosable and non-diagnosable PCG signals from subjects having both normal and abnormal cardiac health. In an embodiment, physionet Challenge 2016 dataset have been used. At step 204, the captured PCG signal is then preprocessed using the preprocessing module 110. The preprocessing of the PCG signal involves down sampling the PCG signal, low pass filtering the down sampled PCG signal using $2^{nd}$ order low pass Butterworth filter, transforming the filtered PCG signal, followed by auto correlating the transformed PCG signal and finally again filtering using the $2^{nd}$ order low pass Butterworth filter.

In the next step 206, a plurality of features are extracted from the preprocessed PCG signal. The set of features used in an embodiment of the disclosure are provide in table I and table II. In the next step 208, the extracted plurality of features are ranked according to their minimum redundancy maximum relevance (mRMR) strength using the mRMR algorithm. At step 210, the irrelevant and redundant features out of the plurality of features are rejected based on a predefined criteria. The predefined criteria is explained in the later part of disclosure with the help of FIG. 7. The remaining features form a first set of features of the PCG signal which are relevant. In the next step 212, the training model is generated using the first set of features.

In the next step 214, the phonocardiogram (PCG) signal is captured from a person using the PCG sensor 102. The PCG sensor 102 can be digital stethoscope used in conjunction with a smartphone. Use of any digital communication device or any other PCG sensor is well within the scope of this disclosure. At step 216, the PCG signal is then preprocessed using the preprocessing module (110). At step 218, the first set of features are extracted from the preprocessed PCG signal. And finally at step 220, the PCG signal is classified as diagnosable or non-diagnosable using the extracted first set of features and a random forest classifier, wherein the random forest classifier is pre-trained using the training model.

According to an embodiment of the disclosure, the system 100 can be explained with the help of the following experimental findings. For the experimental purpose, the same set of plurality of features are used as mentioned above. The training model is generated using the Physionet Challenge 2016.

Experimental Results

A. Evaluation Results

Figure 7:
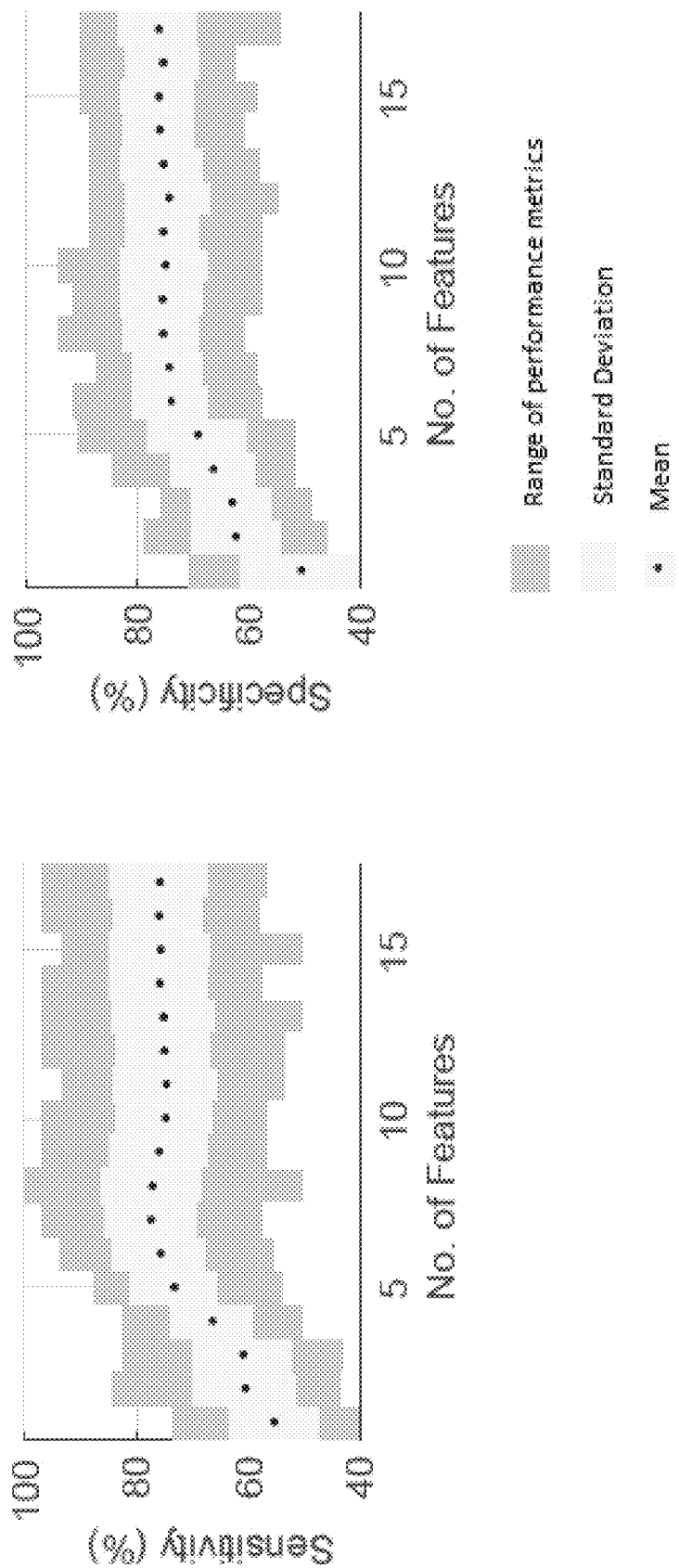
FIG. 7 shows mean, standard deviation and range of performance metrics for cross-validation across all 5 folds over all 16 validation datasets, with number of features (n)=1 to 17 according to an embodiment of the disclosure.

The classification method mentioned above is iterated 16 times, each time with an expanding feature set. Thus the $4^{th}$ ($n^{th}$) iteration uses the top 4 (n) features, numbered 15, 17, 6 and 16 (Table III). Performance metrics, for all cases n=1 to 17, are plotted in FIG. 7. FIG. 7 shows Mean (point), standard deviation (light) and range (dark) of performance metrics for cross-validation across all 5 folds over all 16 validation datasets, with number of features (n)=1 to 17. Sensitivity (Se) is the fraction of clean PCGs and specificity (Sp) is the fraction of noisy PCGs that have been correctly identified. Accuracy (Acc) is defined as (Se+Sp)/2, to compensate for the class imbalance in the testing set. It was concluded from FIG. 4, that the top 11 features (indices 15, 17, 6, 16, 8, 5, 4, 12, 10, 11 and 14) thus constitute the optimum feature set. This set includes 6 of the 7 new features introduced in the present embodiment.

B. Final Predictor

The final Random Forest to be used as a classifier is trained by a dataset created by randomly selecting recordings from clean class to create a balanced set of clean and noisy recordings. This predictor is then used to estimate the quality of the testing data collected on smartphone. This too is repeated to study the effect of changing the training data on the predictor.

C. Test Results

Selection of the optimum feature set involves studying the internal evaluation performances from FIG. 4 and selecting the lowest value of n such that the performance is balanced and high, while the range and standard deviation are low. Proceeding thus, it was found that the optimum feature set for best performance, in terms of Sp, is at n=11, while the same in terms of Se is at n=12. However, the focus should be more on rejecting noisy data perfectly, i.e. to maximize Sp. So Se was trade-off in favor of Sp and select n=11. 16 predictor models were trained using all balanced training sets and tested on the fixed, hidden testing set collected from the local hospital. The final results reported average Se, Sp and Acc across all 16 training models as 88.28%, 66.67% and 75.31% respectively. The results provide a proof of concept that the proposed workflow can achieve true sensor agnosticism. This predictor was also tested on 20 random recording (pseudo-periodic to mimic heart sounds, periodic and aperiodic) none of which were PCGs. All such recordings were correctly identified as noisy, thus proving that the predictor only accepts true PCGs and rejects all the rest.

A predictor was trained using the entire unbalanced (16:1) training set and then tested on the hidden testing set. The Se and Sp were 100% and 0% respectively, because the training set had an overwhelming majority of clean PCGs. This result justifies the use of balanced training datasets.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein addresses unresolved problem of noise in PCG signal, inconsistent quality of the PCG signal etc. which hinders further analysis regarding cardiac health. The embodiment, thus provides a system and method for classifying the PCG signal quality as diagnosable or non-diagnosable.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments may include a hardware configuration of an information handling/computer system in accordance with the embodiments herein. The system herein comprises at least one processor or central processing unit (CPU). The CPUs are interconnected via system bus to various devices such as a random access memory (RAM), read-only memory (ROM), and an input/output (I/O) adapter. The I/O adapter can connect to peripheral devices, such as disk units and tape drives, or other program storage devices that are readable by the system. The system can read the inventive instructions on the program storage devices and follow these instructions to execute the methodology of the embodiments herein.

The system further includes a user interface adapter that connects a keyboard, mouse, speaker, microphone, and/or other user interface devices such as a touch screen device (not shown) to the bus to gather user input. Additionally, a communication adapter connects the bus to a data processing network, and a display adapter connects the bus to a display device which may be embodied as an output device such as a monitor, printer, or transmitter, for example.

The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

What is claimed is:

1. A method for classifying phonocardiogram (PCG) signal quality, the method comprising a processor (106) implemented steps of:
   providing a training dataset, wherein the training dataset comprises a plurality of sample PCG signals covering a plurality of scenarios of diagnosable and non-diagnosable PCG signals from subjects having both normal and abnormal cardiac health;
   preprocessing the training dataset using a preprocessing module (110);
   extracting a plurality of features from the preprocessed training dataset using a feature extraction module (114);
   ranking the extracted plurality of features according to their minimum redundancy maximum relevance (mRMR) strength using an mRMR algorithm;
   rejecting the irrelevant and redundant features out of the plurality of features based on a predefined criteria, wherein the remaining features form a first set of features of the PCG signal which are relevant;
   generating a training model using the first set of features;
   capturing the phonocardiogram (PCG) signal from a person under test using a PCG sensor (102);
   preprocessing the PCG signal using the preprocessing module (110);

extracting the first set of features from the preprocessed PCG signal; and classifying the PCG signal as diagnosable or non-diagnosable using the first set of features and a random forest classifier, wherein the random forest classifier is pre-trained using the training model.

2. The method of claim 1, wherein the step of preprocessing the PCG signal comprises:

down sampling the PCG signal;

filtering the down sampled PCG signal using a $2^{nd}$ order Butterworth low pass filer at a frequency of about 20 Hz;

applying Hilbert transform on the filtered PCG signal;

auto-correlating the transformed PCG signal; and filtering the auto-correlated PCG signal using a $2^{nd}$ order Butterworth low pass filter at the frequency of about 10 Hz.

3. The method of claim 1, wherein the plurality of features include one or more of:

a sample entropy of the auto-correlated PCG signal,

Kurtosis of the auto-correlated PCG signal, minimum ratio of the second to first singular value from the singular value decomposition (SVD) of varying window sizes of the auto-correlated PCG signal, a signal power of the auto-correlated PCG signal, variance of the auto-correlated PCG signal, correlation coefficient between the auto-correlated PCG signal and a fitted sum of rectified sinusoids, and correlation coefficient between the auto-correlated PCG signal and a fitted sum of rectified and decaying sinusoids.

4. The method of claim 1 wherein the plurality of features further includes a plurality of spectral features derived from the PCG signal, wherein the plurality of spectral features comprises:

ratio of power contained in 0-240 Hz to the power contained in 240-1000 Hz, mean and variance of spectral energy of overlapping frames, mean and variance of spectral flux computed between overlapping frames, mean and variance of ratio of power contained in 0-500 Hz to the remaining power for overlapping frames, and mean and maximum of mean power spectral density for overlapping frames.

5. The method of claim 1 wherein the step of classifying is configured to give an output value as '0' if the PCG signal is non-diagnosable and as '1' if the PCG signal is diagnosable.

6. The method of claim 1, wherein the PCG sensor (102) is a stethoscope and the PCG signal is captured on a smartphone.

7. The method of claim 1 further include the step of sending the output value to a user of the PCG sensor (102) as feedback.

8. A system (100) for classifying phonocardiogram (PCG) signal quality, the system comprises:

a memory (104);

a processor (106) in communication with the memory (104), the processor (106) further comprises:

an input module (122) providing a training dataset, wherein the training dataset comprises a plurality of sample PCG signals covering a plurality of scenarios of diagnosable and non-diagnosable PCG signals from subjects having both normal and abnormal cardiac health;

a preprocessing module (110) for preprocessing the training dataset;

a feature extraction module (114) for extracting a plurality of features from the training dataset;

a ranking module (116) for ranking the extracted plurality of features according to their minimum redundancy maximum relevance (mRMR) strength using an mRMR algorithm, the ranking module (116) further configured to reject the irrelevant and redundant features out of the plurality of features based on a predefined criteria, wherein the remaining features form a first set of features of the PCG signal which are relevant; and a training model generation module (118) for generating the training model using the first set of features;

a PCG sensor (102) capturing the phonocardiogram (PCG) signal from a person under test, wherein the PCG signal is preprocessed using the preprocessing module (110), and the first set of features are extracted from the preprocessed PCG signal; and a classification module (118) classifying the PCG signal as diagnosable or non-diagnosable using the extracted first set of features and a random forest classifier, wherein the random forest classifier is pre-trained using the training model.

9. A system for monitoring the cardiac health using a phonocardiogram (PCG) signal of a person, the system comprises:

a memory (104);

a processor (106) in communication with the memory (104), the processor (106) further comprises:

an input module (122) providing a training dataset, wherein the training dataset comprises a plurality of sample PCG signals covering a plurality of scenarios of diagnosable and non-diagnosable PCG signals from subjects having both normal and abnormal cardiac health;

a preprocessing module (110) for preprocessing the training dataset;

a feature extraction module (114) for extracting a plurality of features from the training dataset;

a ranking module (116) for ranking the extracted plurality of features according to their minimum redundancy maximum relevance (mRMR) strength using an mRMR algorithm, the ranking module (116) further configured to reject the irrelevant and redundant features out of the plurality of features based on a predefined criteria, wherein the remaining features form a first set of features of the PCG signal which are relevant; and a training model generation module (118) for generating the training model using the first set of features;

a PCG sensor (102) capturing the phonocardiogram (PCG) signal from a person under test, wherein the PCG signal preprocessed using the preprocessing module (110), and the first set of features are extracted from the preprocessed PCG signal using the feature extraction module (114);

a classification module (118) classifying the PCG signal as diagnosable or non-diagnosable using the extracted first set of features and a random forest classifier, wherein the random forest classifier is pre-trained using the training model; and a cardiac health detection module (120) for detecting the health of the person using only diagnosable PCG signal as classified by the classification module.

10. One or more non-transitory machine readable information storage mediums comprising one or more instructions which when executed by one or more hardware processors perform actions comprising:
- providing a training dataset, wherein the training dataset comprises a plurality of sample PCG signals covering a plurality of scenarios of diagnosable and non-diagnosable PCG signals from subjects having both normal and abnormal cardiac health;
- preprocessing the training dataset using a preprocessing module (110);
- extracting a plurality of features from the preprocessed training dataset using a feature extraction module (114);
- ranking the extracted plurality of features according to their minimum redundancy maximum relevance (mRMR) strength using an mRMR algorithm;
- rejecting the irrelevant and redundant features out of the plurality of features based on a predefined criteria, wherein the remaining features form a first set of features of the PCG signal which are relevant;
- generating a training model using the first set of features;
- capturing the phonocardiogram (PCG) signal from a person under test using a PCG sensor (102);
- preprocessing the PCG signal using the preprocessing module (110);
- extracting the first set of features from the preprocessed PCG signal; and
- classifying the PCG signal as diagnosable or non-diagnosable using the first set of features and a random forest classifier, wherein the random forest classifier is pre-trained using the training model.

11. The one or more non-transitory machine readable information storage mediums of claim 10, wherein the step of preprocessing the PCG signal comprises:
- down sampling the PCG signal;
- filtering the down sampled PCG signal using a $2^{nd}$ order Butterworth low pass filer at a frequency of about 20 Hz;
- applying Hilbert transform on the filtered PCG signal;
- auto-correlating the transformed PCG signal; and
- filtering the auto-correlated PCG signal using a $2^{nd}$ order Butterworth low pass filter at the frequency of about 10 Hz.

12. The one or more non-transitory machine readable information storage mediums of claim 10, wherein the plurality of features include one or more of:
- a sample entropy of the auto-correlated PCG signal,
- Kurtosis of the auto-correlated PCG signal,
- minimum ratio of the second to first singular value from the singular value decomposition (SVD) of varying window sizes of the auto-correlated PCG signal,
- a signal power of the auto-correlated PCG signal,
- variance of the auto-correlated PCG signal,
- correlation coefficient between the auto-correlated PCG signal and a fitted sum of rectified sinusoids, and
- correlation coefficient between the auto-correlated PCG signal and a fitted sum of rectified and decaying sinusoids.

13. The one or more non-transitory machine readable information storage mediums of claim 10, wherein the plurality of features further includes a plurality of spectral features derived from the PCG signal, wherein the plurality of spectral features comprises:
- ratio of power contained in 0-240 Hz to the power contained in 240-1000 Hz,
- mean and variance of spectral energy of overlapping frames,
- mean and variance of spectral flux computed between overlapping frames,
- mean and variance of ratio of power contained in 0-500 Hz to the remaining power for overlapping frames, and
- mean and maximum of mean power spectral density for overlapping frames.

14. The one or more non-transitory machine readable information storage mediums of claim 10, wherein the step of classifying is configured to give an output value as '0' if the PCG signal is non-diagnosable and as '1' if the PCG signal is diagnosable.

15. The one or more non-transitory machine readable information storage mediums of claim 10, wherein the PCG sensor (102) is a stethoscope and the PCG signal is captured on a smartphone.

16. The one or more non-transitory machine readable information storage mediums of claim 10, further include the step of sending the output value to a user of the PCG sensor (102) as feedback.

* * * * *